United States Patent [19]

Casciani

[11] Patent Number: 4,960,536

[45] Date of Patent: Oct. 2, 1990

[54] CARBOXYALKYLATED DERIVATIVES OF ALKYL AND ALKENYL CATECHOL ETHOXYLATES AND DETERGENT COMPOSITIONS CONTAINING SAME

[75] Inventor: Robert V. Casciani, Charlotte, N.C.

[73] Assignee: Sandoz Ltd., Basel, Switzerland

[21] Appl. No.: 321,421

[22] Filed: Mar. 9, 1989

[51] Int. Cl.$^5$ .......................... C07C 59/71; C11D 1/06
[52] U.S. Cl. .............................. 252/174.19; 252/89.1; 252/174.21; 562/471
[58] Field of Search ............. 252/89.1, 174.21, 174.19; 562/471

[56] References Cited

U.S. PATENT DOCUMENTS

| | | | |
|---|---|---|---|
| 4,194,565 | 3/1980 | Kalfoglou | 166/275 |
| 4,242,215 | 12/1980 | Smid et al. | 252/100 |
| 4,855,075 | 8/1989 | Casciani | 252/174.21 |

FOREIGN PATENT DOCUMENTS 926898  5/1963  United Kingdom .

*Primary Examiner*—Prince E. Willis
*Attorney, Agent, or Firm*—Gerald D. Sharkin; Robert S. Honor; Joseph J. Borovian

[57] ABSTRACT

The invention relates to novel carboxyalkylated derivatives of alkyl and alkenyl catechol ethoxylates and to their use as surface active agents. The novel carboxyalkylated derivatives are especially useful as self-sequestering surfactants in detergent compositions.

19 Claims, No Drawings

CARBOXYALKYLATED DERIVATIVES OF ALKYL AND ALKENYL CATECHOL ETHOXYLATES AND DETERGENT COMPOSITIONS CONTAINING SAME

This invention relates to a new class of surface active agents. More particularly, it relates to novel carboxyalkylated derivatives of alkyl and alkenyl catechol ethoxylates and to their use as surface active agents, and more especially to their use as dual action surfactants, hereinafter referred to as self-sequestering surfactants.

Synthetic surface active agents, e.g., detergents, can be characterized as compounds which incorporate within the molecular structure thereof a hydrophobic moiety, typically a long-chain alkyl moiety, and also a hydrophilic moiety which, because of being polar in character or having ionic charge, is capable of interaction with water molecules. When the hydrophilic moiety is characterized by a formal ionic charge, the surface active agent is classified as anionic or cationic, depending upon the nature of the ionic charge. Alternatively, if the hydrophilic moiety does not possess a formal ionic charge, the surface active agent is termed a non-ionic surface active agent. One frequently encountered class of non-ionic surface active agents comprises alkylene oxide derivatives of active hydrogen compounds, particularly the alkylene oxide derivatives of fatty acids or long-chain alcohols. However, since the available supply of natural fatty acids and alcohols does not always coincide with the demands of the surface active agent industry, such products are subject to extremely large price fluctuations and, as a consequence thereof, exhibit severe economic shortcomings.

As is well known in the art, the detergent properties of conventional surfactants are considerably reduced when such surfactants are employed in hard water. The reduction in detersive properties is due to the presence of multivalent ions, such as calcium and magnesium cations, in the water. To overcome this problem, it is well known to add a sequestering compound to the detergent composition, the primary function of which is to form a complex with the multivalent ions of the water and thereby compensate for the disadvantage of employing hard water.

Of the known sequestering compounds, some exhibit additional properties besides that of complexing with multivalent ions in hard water. Thus, some sequestering compounds, more commonly referred to as "builders", enhance (a) the stabilization of suspended solids; (b) the emulsification of dirt particles; (c) the activity of surface active agents; and (d) the solubilization of water-insoluble materials. Moreover, most of the known sequestering compounds are compatible with the other conventional components present in detergent compositions. However, a large number of sequestering compounds, e.g., sodium tripolyphosphate and nitrilotriacetic acid, have the serious drawback of causing eutrofication phenomena, and thereby adversely affect the environment.

Other sequestering compounds, e.g., those based on alkaline carbonates and polysilicates exhibit rather serious caustic and toxic effects, thereby diminishing their usefulness appreciably.

A further disadvantage of conventional detergent compositions, i.e., those containing both a surface active agent and a sequestering compound, is that a separate synthesis is required for the two different compounds, which compounds are then mixed in various proportions, depending upon their ultimate use.

Accordingly, it is an object of the present invention to provide a new class of surface active agents. It is another object of the present invention to provide a new class of surface active agents which exhibit a dual action, thereby making them useful as self-sequestering surfactants. It is still another object of the present invention to provide a new class of self sequestering surfactants which are especially useful when employed in hard water. It is a further object of the present invention to provide a new class of self-sequestering surfactants which, when employed in hard water, are surprisingly useful at low concentrations of the multivalent ions in the water. It is yet still another object of the present invention to provide a new class of self-sequestering surfactants which, when employed in hard water, neither contribute to eutrofication, nor exhibit any serious caustic or toxic effect.

The attainment of the above objects is made possible by certain carboxyalkylated derivatives of alkyl and alkenyl catechol ethoxylates of formula I:

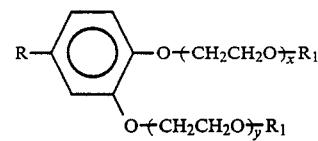

wherein,

R is $C_8$-$C_{22}$ straight or branched chain alkyl or alkenyl;

each $R_1$, independently, is hydrogen or a group —$R_2$COOM, where $R_2$ is $C_{1-3}$ alkylene and M is hydrogen, an alkali metal cation, an alkaline earth metal cation or ammonium; and each of x and y is, independently, an integer 1 to 49; with the provisos that: (1) at least one of the $R_1$'s is a group —$R_2$COOM; and (2) the sum of x and y is 3 to 50.

R is preferably straight or branched chain alkyl having from 8 to 22 atoms, more preferably 8 to 14 carbon atoms, and even more preferably from 8 to 12 carbon atoms.

$R_2$ is —$CH_2$—, —$CH_2CH_2$—, —$CH_2CH_2CH_2$—,

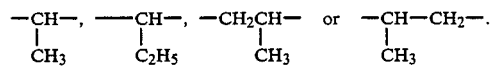

Preferably, $R_2$ is —$CH_2$, —$CH_2CH_2$— or —$CH_2CH_2CH_2$—. More preferably, $R_2$ is —$CH_2$—.

The preferred alkali metals as M are sodium, potassium and lithium, more preferably sodium and potassium. The preferred alkaline earth metals as M are magnesium, calcium, barium and strontium, more preferably magnesium and calcium. M is preferably hydrogen, an alkali metal or ammonium, more preferably hydrogen, sodium, potassium or ammonium, and even more preferably hydrogen.

The variables x and y are preferably each, independently, an integer 1 to 29, with the proviso that the sum of x and y is 3 to 30. The variables x and y are more preferably each, independently, an integer 1 to 19, with the proviso that the sum of x and y is 3 to 20. The variables x and y are even more preferably each, independently, an integer 1 to 14, with the proviso that the sum of x and y is 3 to 15.

The preferred compounds of formula I are those of formula Ia:

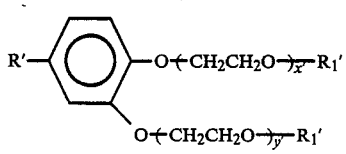

wherein

R' is $C_8$—$C_{22}$ straight or branched chain alkyl;

each $R_1'$, independently, is hydrogen or a group —$R_2COOM$, where $R_2$ is —$CH_2$—, —$CH_2CH_2$— or —$CH_2CH_2CH_2$— and M is hydrogen, an alkali metal or ammonium; and each of x' and y' is, independently, an integer 1 to 29, with the provisos that: (1) at least one of the $R_{13}$'s is a group —$_2COOM$; and (2) the sum of x' and y' is 3 to 30.

The more preferred compounds of formula I are those of formula Ib:

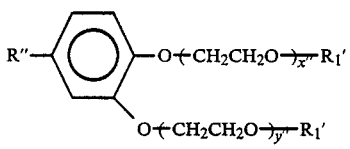

wherein

R" is $C_8$–$C_{14}$ straight or branched chain alkyl;

each $R_1"$, independently, is hydrogen or a group —$CH_2COOM$, where M is hydrogen, sodium, potassium or ammonium; and each of x" and y" is, independently, an integer 1 to 19, with the provisos that: (1) at least one of the $R_1"'$'s is a group -$CH2COOM$; and (2) the sum of x" and y" is 3 to 20.

The even more preferred compounds of formula I are those of formula Ic:

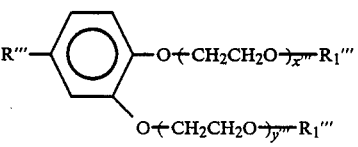

wherein

R" is $C_8$-$C_{12}$ straight or branched chain alkyl;

each R1", *independently, is hydrogen or a group* —$CH_2COOH$; and each of x''' and y''' is, independently, an integer 1 to 14, with the provisos that: (1) at least one of the $R_1""$'s is a group —$CH_2COOH$; and (2) the sum of x''', and y''' is 3 to 15.

The compounds of formula I are produced by more or less conventional methods. Thus, the novel carboxyalkylated derivatives of the alkyl and alkenyl catechol ethoxylates may be prepared by condensing the appropriate alkyl or alkenyl catechol compound with ethylene oxide by the well-known methods of adding alkylene oxide compounds to an alcohol. Suitable results are obtained by adding to the alkyl or alkenyl catechol compound to be ethoxylated a catalytic amount, e.g., from about 0.2% to 1%, preferably 0.3% to 0.75%, by weight of the total amount of reactants, including the respective alkylene oxides, of an alkaline catalyst. Catalysts which may be employed include alkali metal hydroxides, sodium ethoxide, sodium methoxide, alkali metal acetates and dimethylamine, and mixtures thereof. Preferred catalysts are the alkali metal hydroxides, more preferably sodium hydroxide and potassium hydroxide. Other types of catalysts commonly used for alkylene oxide condensation reactions may also be employed.

Optionally, a small amount of a reducing agent may be added to the alkyl or alkenyl catechol compound to be ethoxylated to minimize discoloration of the resulting ethoxylated alkyl or alkenyl catechol compound. Suitable reducing agents which may be employed include sodium borohydride, lithium aluminum hydride, diborane and the like, preferably sodium borohydride.

An amount of ethylene oxide calculated to provide the desired degree of ethoxylation is then introduced and the resulting mixture is allowed to react until all of the ethylene oxide is consumed, as indicated by a drop in reaction pressure. Customarily, the ethoxylated product is finally treated with weak acid, e.g., glacial acetic acid, to neutralize any basic catalyst residues.

It should be understood that the ethoxylation procedure serves to introduce a desired average number of ethylene oxide units per catechol molecule. Thus, for example, the treatment of an alkyl or alkenyl catechol compound with x moles of ethylene oxide per mole of catechol compound serves to effect the ethoxylation of each alcohol moiety with ethylene oxide to an average of x ethylene oxide moieties per alcohol moiety, although some alcohol moieties will have become combined with more than x ethylene oxide moieties and some will have become combined with less than x. The variation in the number of ethylene oxide moieties is not critical as long as the average for the number of units in each block is within the limits set out for the x and y terms in formula I above, which terms, as average values, are other than whole numbers in some instances.

The ethoxylation procedure is conducted at an elevated temperature and pressure. Suitable reaction temperatures are from about 120° C. to about 220° C., preferably 130° C. to 180° C., and more preferably 140° C. to 160° C. A suitable reaction pressure is achieved by introducing to the reaction vessel the required amount of ethylene oxide which has a high vapor pressure at the desired reaction temperature. The pressure serves as a measure of the degree of reaction and the ethoxylation is considered to be complete when the pressure no longer decreases with time.

For best results, it is desirable to carry out the ethoxylation under relatively moisture-free conditions and to avoid side reactions which form water. To dry the reaction vessel and connection, they may be swept out with a dry, oxygen-free gas, e.g., nitrogen, before introducing the charge. The catalyst or catalyst mixture should also be dry, or substantially so. The ethylene oxide should preferably be purified to remove moisture and any impurities which are capable of entering into side reactions which yield water.

To prepare the corresponding carboxyalkylated derivatives, the resulting alkyl and alkenyl catechol ethoxylates are then carboxyalkylated by the Williamson synthesis, involving reaction with an appropriate chloro- or bromocarboxylic acid or a salt thereof in the presence of a strong base, e.g., sodium hydroxide, sodium carbonate, etc., or a mixture thereof, metallic sodium, or by catalytic oxidation. The carboxyalkylation is conducted at a temperature of between 20° and 100° C., preferably between 50° and 90° C., and at a mole ratio of between 0.5:1 and 2.5:1 preferably between 1:1 and 2:1 of chloro- or bromocarboxylic acid or a salt thereof, e.g., sodium monochloroacetate, to alkyi or alkenyl catechol ethoxylate. Such reactions are ordinarily not complete; hence, the reaction products often contain minor amounts of uncarboxylated alkyl or alkenyl catechol ethoxylate. While methods are available for separating the uncarboxylated material as well as for assuring essentially complete carboxyalkylation, they are usually tedious and expensive. Fortunately, it has been found that minor proportions of such uncarboxyalkylated material are not particularly harmful, and may even be advantageous. The carboxyalkylation involving reaction with an appropriate chloro- or bromocarboxylic acid or a salt thereof in the presence of a strong base is preferred for completeness. Preferably, the carboxyalkyl group is a carboxymethyl group.

Alternatively, the corresponding carboxyalkylated derivatives of formula I wherein $R_2$ is $-CH_2CH_2-$ may be prepared via base catalyzed 1,4-addition to an appropriate $\alpha, \beta$-unsaturated compound such as methyl acrylate or acrylamide followed by hydrolysis. Moreover, the corresponding carboxyalkylated derivatives of formula I wherein $R_2$ is $-CH_2CH_2CH_2-$ may be prepared by a reaction involving alkoxylate addition to an appropriate lactone which yields the corresponding carboxylate.

The most conspicuous property of the compounds of formula I is their great activity at surfaces and interfaces, making them especially useful as surface active agents. The uses to which surface active agents can be put are numerous and well known and, as a result, the possible applications of these new compounds are extremely varied. Thus, the surface active agents of the present invention are suitable as emulsifiers, dispersing agents, wetting agents, levelling agents and the like in the textile, leather, paper, lacquer, personal care, e.g., toiletries, cosmetics, etc., and rubber industries. For example, they can be used as wetting agents in spinning, twisting, weaving and dyeing operations in the textile industry, especially in the presence of hard water. In addition, they can be utilized for converting liquid or solid substances which, per se, are insoluble in water (such as hydrocarbons, higher alcohols, oils, fats, waxes and resins) into creamy emulsions, clear solutions or fine, stable dispersions.

Moreover, the compounds of formula I are valuable emulsifiers for insecticide compositions and agricultural sprays such as DDT, 2,4-D and the like; are valuable for use as additives to petroleum products, hydraulic fluids, lubricating oils, cutting oils and greases; may be employed as coating aids for use in coating compositions comprising a hydrophilic, film-forming colloid; may be employed as tackifiers in the adhesive layer of adhesive tapes in, e.g., the photographic industry; and as foaming agents and dispersing agents in a wide variety of mining applications (i.e., or flotation).

Furthermore, because of their ability to complex metal ions, the compounds of formula I can be used to remove heavy metal contaminants from waste water. These materials are especially useful in this context due to their surface active properties. Therefore, processes such as solvent extraction can be facilitated by utilizing the compounds of the instant invention.

The carboxyalkylated derivatives of the instant invention are especially useful as self-sequestering surfactants in detergent compositions. Thus, in view of their detersive properties, they may be employed as the sole surfactant component in said detergent compositions and, as a result of their sequestering capabilities, they may be employed as the sole sequestering component, i.e., the detergent compositions need not contain a different and separate sequestering compound. As self-sequestering surfactants, the carboxyalkylated derivatives of the instant invention form soluble complexes with calcium and magnesium cations sufficiently stable to eliminate the negative influences on the detersive properties of the compositions but not so stable as to cause ecological imbalance because of an accumulation of ions. Such detergent compositions will normally contain from at least 5% to about 50% of said alkyl or alkenyl catechol ethoxylate, preferably from about 10% to about 50%, and more preferably from about 15% to about 50%.

The carboxyalkylated derivatives of the instant invention, because of their self-sequestering properties, can advantageously be employed in detergent compositions which already contain a conventional surfactant, e.g., an anionic, nonionic, ampholytic or zwitterionic surfactant, or mixtures thereof, coupled with the additional advantage that, as compared with other known sequestering compounds under equal conditions, such detergent compositions exhibit greater detersive capability without concomitant harmful environmental effects or any other drawbacks and disadvantages of the known sequestering compounds. Representative anionic surfactants are:

(1) alkylbenzenesulfonates, such as sodium and potassium salts having a branched or straight chain alkyl portion of about 9 to about 15 carbon atoms; (2) alkyl sulfates, such as the sodium and triethanolammonium salts of $C_{10-20}$ alkyl sulfuric acids, prepared by sulfating the alcohols derived from coconut oil or tallow, or prepared synthetically; (3) the alkali metal and ammonium salts of the sulfated ethoxylates of a long-chain alcohol and 3 to 5 molar; proportions of ethylene oxide, e.g., the ammonium salt of an ethoxylate containing an average of 3.1 molar proportions of ethylene oxide and 1 mole of an alcohol mixture known, commercially as ALFOL 1412, composed of about 2/3 n-tetradecanol and about 1/3 n-dodecanol; (4) the compounds known as "Medialans" which are amido carboxylic acids formed by condensing fatty acids of $C_{8-22}$ chain length with sarcosine, $CH_3NHCH_2COOH$; (5) alkanesulfonates, such as ammonium dodecanesulfonate; (6) alkoxyhydroxypropanesulfonates, such as the water-soluble salts of 3-dodecyloxy-2-hydroxy-1-propane-sulfonate; (7) soaps, the surface-active substances formed usually by the reaction of caustic alkalies with natural glyceridic fats and oils, generally prepared in high purity, and having the generic molecular formula RCOONa, wherein R is a straight-chain hydrocarbon group having from about 7 to about 21 carbon atoms; and (8) olefin sulfonates, such as dodecene sulfonate, and the compounds described in U.S. Pat. No. 3,332,880. As representative of non-ionic surfactants may be mentioned: (1) the Pluronios, formed by condensing propylene oxide with propylene glycol to a molecular weight of about 600 to 2500 to form a base followed by condensing ethylene oxide to this base to the extent of about 10 to about 90 percent, total molecule basis U.S. Pat. Nos. 2,674,619 and 2,677,700 describe operable compounds; (2) compounds formed by the simultaneous polymerization of propylene oxide and ethylene oxide and containing randomly positioned oxypropylene and oxyethylene groups. These and related compounds are described in U.S. Pat. Nos. 2,979,528, 3,036,118, 3,022,335, 3,036,130 and U.S. Pat. No. 3,048,548; (3) alkyl phenols having 9 to 12 carbon atoms in the alkyl portion (straight or branched) ethoxylated with 4-10 molar proportions of ethylene oxide; and (4) ethoxylates of fatty alcohols having 8 to 18 carbon atoms per molecule and 5-30 molar proportions of oxyethylene groups.

As an example of an ampholytic surfactant may be mentioned the hydroxyalkyl methyl taurates, while cocodimethyl sulfopropyl betaine is exemplary of a zwitterionic surfactant.

In detergent compositions which contain a carboxyalkylated derivative of the instant invention and a conventional surfactant, the latter will normally comprise between 5% and 40% of the weight of the mixture, preferably between 10% and 30%.

When the self-sequestering compounds of the instant invention are employed in detergent compositions which contain a different and separate sequestering compound having one or more of the above-discussed drawbacks and disadvantages, the concentration of the different sequestering compound can be reduced, thereby reducing the toxic and polluting properties of said different sequestering compound. Representative inorganic sequestering compounds are, e.g., water soluble salts of pyrophosphates, orthophosphates, polyphosphates, phosphonates, carbonates, bicarbonates and silicates. As representative of organic sequestering compounds may be mentioned the alkali metal, ammonium and substituted ammonium polyacetates, carboxylates, polycarboxylates and polyhydroxy-sulfonates.

In detergent compositions which contain a carboxyalkylated derivative of the instant invention and a different and separate sequestering compound, the latter will normally comprise between 5 and 60% of the weight of the mixture, preferably between 10% and 40%.

The detergent compositions can optionally contain all manner of additional materials commonly found in laundering and cleaning compositions. For example, oxidizing bleaches such as sodium perborate, sodium percarbonate, etc., optionally with bleach precursors such as phthalic anhydride, may be incorporated at levels of 1% to 25% of the composition. When these materials are present, the compounds of formula I can also serve as peroxide stabilizers. Their ability to sequester certain metal ions will serve to prevent the undersired decomposition of these oxidizing agents.

Defoamers such as long chain fatty acids, silicone fluids and microcrystalline waxes may be employed alone or as mixtures at levels of 0.005% to 5%, preferably 0.01% to 3%, and most preferably 0.1% to 1%, of the composition.

Viscosity modifiers and anticaking agents such as the sodium salts of lower alkyl aromatic sulfonic acids and the alkali metal salts of sulfosuccinic acid and benzene sulfonic acid are conveniently employed at levels of 0.5% to 5%, particularly if other anionic surfactants are employed as part of the surfactant mixture.

Soil suspending agents such as sodium carboxymethyl cellulose and hydroxyethyl cellulose may also be used in amounts of 0.25% to 5% by weight of the composition.

Enzymes such as the proteolytic enzymes may be incorporated at levels of up to 1% by weight, preferably from 0.25% to 0.75% by weight. Such enzymatic materials may be coated or pilled to aid their stability and to minimize the formation of dust during processing and subsequent storage.

The following examples illustrate the preparation of the carboxyalkylated derivatives of the instant invention.

EXAMPLE 1

Dodecaethoxy nonylcatechol acetic acid

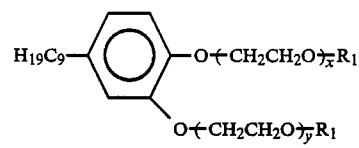

where $x+y=12$; and the sum of the $R_1$'s $=-CH_2COOH$ (66%); -H (34%).

(a) Preparation of nonylcatechol

Into a 500ml, 3-neck reaction vessel was placed 64.8g (0.3125 moles) of catechol, after which time it was heated to 104° C. under a nitrogen flow. After the catechol was completely melted, 3.25g (5% based on the wt. of the catechol) of borontrifluoride-etherate was added dropwise, with stirring. After adding all of the catalyst, 63.2 g (0.25 moles) of 1-nonene was added dropwise to the reaction mixture, the rate of addition being adjusted so as to maintain a temperature of 130° C. After all of the 1-nonene was added, the resultant mixture was allowed to react for 3 hours, after which time 100 ml of a 10% sodium chloride solution was added to the reaction mixture. The resultant mixture was then stirred for 15 minutes at 95° to 100° C., after which time the bottom layer was separated. The mixture was again stirred at 95° to 100° C. for 15 minutes, after which time the bottom layer was again separated. The organic layer was then isolated to obtain a viscous, brown oil of the formula

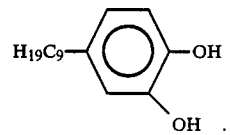

(b) Preparation of dodecaethoxy nonylcatechol

Into a reaction vessel containing 62 g of the compound prepared in a) above was added, with stirring, 0.1 g of sodium hydroxide catalyst. The system was then purged with nitrogen, evacuated and the temperature raised to 120° C., after which time the system was again purged and evacuated. The purging and evacuation procedure is then repeated twice more at 120° C, after which time the temperature of the reaction mixture was raised to 155° C. 140 g of ethylene oxide was then added to the reaction mixture at a rate such that a constant pressure was maintained. When the addition of ethylene oxide is complete, the reaction mixture is allowed to post-react until the pressure drops to a point where it remains constant for at least 30 minutes. The system is then cooled to 60° C. and the vacuum broken with nitrogen. The remaining sodium hydroxide catalyst is then neutralized with acetic acid, after which time the reaction mixture is cooled and filtered to yield a compound of the formula

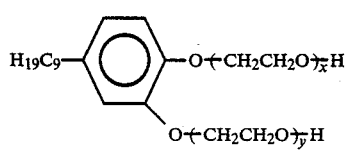

where x+y=12.

Preparation of the title compound 76.5 g of the compound prepared in (b) above was placed into a 3-neck reaction vessel equipped with a condensor, mechanical stirrer and thermometer. To the flask was added, sequentially with stirring, 5.3 g of potassium hydroxide and 3.21 g of sodium hydroxide. The resultant mixture was then stirred for one hour, while the temperature was maintained between 50° and 55° C. 18.7 g of sodium monochloroacetate was then added to the mixture in four equal portions over a two hour period, while the exotherm was controlled to 65°±5° C. After the addition was complete, the reaction was allowed to proceed for 20 hours, after which time the reaction mixture was diluted with 50ml of water and 75ml of a 10% sulfuric acid solution. Phase separation yielded the title compound as an amber oil.

EXAMPLE 2

Following essentially the last step of the procedure in preparing the compound of Example 1b) and utilizing the catechol compound prepared in 1a) and the appropriate amounts of ethylene oxide, the following compounds are obtained:

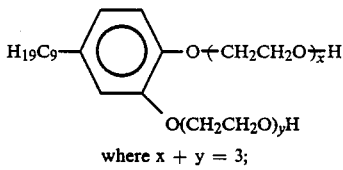

where x + y = 3;

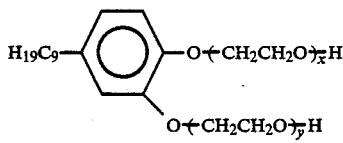

where x + y = 6; and

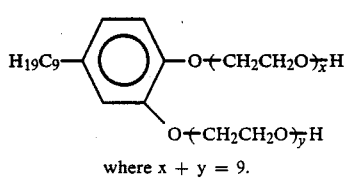

where x + y = 9.

EXAMPLE 3

Triethoxy nonylcatechol acetic acid

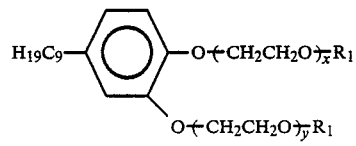

where x+y=3; and the sum of the $R_1$'s=—CH$_2$COOH(47%); —H(53%).

73.7 g of the compound of Example 2a) was placed into a 3-neck reaction vessel equipped with a condensor, mechanical stirrer and thermometer. To the flask was added, sequentially with stirring, 10.56 g of potassium hydroxide and 6.4 g of sodium hydroxide. The resultant mixture was then stirred for one hour, while the temperature was maintained between 50° and 55° C. 37.4 g of sodium monochloroacetate was then added to the mixture in four equal portions over a two hour period, while the exotherm was controlled to 65°+/−5° C. After the addition was complete, the reaction was allowed to proceed for 20 hours, after which time the reaction mixture was diluted with 50ml of water and 75ml of a 10% sulfuric acid solution. Phase separation yielded the title compound as an amber oil.

EXAMPLE 4

Hexaethoxy nonylcatechol acetic acid

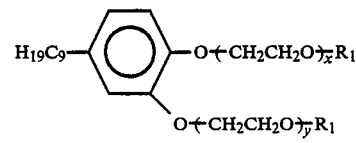

where x+y=6; and the sum of the $R_1$'s=—CH$_2$COOH(52%); —H(48%).

75.0 g of the compound of Example 2b) was placed into a 3-neck reaction vessel equipped with a condensor, mechanical stirrer and thermometer. To the flask was added, sequentially with stirring, 7.9 g of potassium hydroxide and 4.81 g of sodium hydroxide. The resultant mixture was then stirred for one hour, while the temperature was maintained between 50° and 55° C. 28.1 g of sodium monochloroacetate was then added to the mixture in four equal portions over a two hour period, while the exotherm was controlled to 65+/−5° C. After the addition was complete, the reaction was allowed to proceed for 20 hours, after which time the reaction mixture was diluted with 50ml of water and 75ml of a 10% sulfuric acid solution. Phase separation yielded the title compound as an amber oil.

EXAMPLE 5

Nonaethoxy nonylcatechol acetic acid

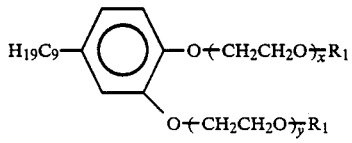

where x+y=9; and the sum of the $R_1$'s=—CH$_2$COOH(58%); —H(42%).

63.2 g of the compound of Example 2c) was placed into a 3-neck reaction vessel equipped with a condensor, mechanical stirrer and thermometer. To the flask was added, sequentially with stirring, 5.3 g of potassium hydroxide and 3.21 g of sodium hydroxide. The resultant mixture was then stirred for one hour, while the temperature was maintained between 50° and 55° C. 18.7 g of sodium monochloroacetate was then added to the mixture in four equal portions over a two hour period, while the exotherm was controlled to 65°±5° C. After the addition was complete, the reaction was allowed to proceed for 20 hours, after which time the reaction mixture was diluted with 50ml of water and 75ml of a 10% sulfuric acid solution. Phase separation yielded the title compound as an amber oil.

It should be understood that in all of the examples above, the indicated number of ethyleneoxy units are average values.

EXAMPLE 6

To demonstrate the ability of the carboxyalkylated derivatives of the instant invention to sequester metal ions, they were evaluated by determining the constants of stability of the complexes formed by the calcium utilizing potentiometric titrations with electrodes selective toward the calcium ion in question. During these titrations, the quantity of calcium ion complexed by a known quantity of sequestering agent was measured and the result of the measurement was used to calculate the constant of the complex (Kca) employing the following equation:

$$Kca = \frac{[\text{Ca tot}] - [\text{Ca free}]}{[\text{Ca free}] \times [\text{L free}]}$$

where L=ligand or sequestrant and [L free]=[L tot]—[Ca tot]+[Ca free]. At high ratios of [Ca tot]/[L tot], the ligand became saturated with Ca ion and a linear increase in [Ca free]resulted. This line was extrapolated back to [Ca free]=0 and [Ca tot]at that point represented a measure of calcium binding capacity. Below are the results obtained on the compound of Example 4:

| [Ca] total | $K_{Ca}$ | log $K_{Ca}$ |
| --- | --- | --- |
| 0.00099 | 134.6 | 2.13 |
| 0.00476 | 41.3 | 1.62 |
| 0.00909 | 21.9 | 1.34 |

From the above results, it is clear that the compound of Example 4 exhibits excellent calcium binding ability. Moreover, it should be noted that the compound of Example 4 exhibits surprising effectiveness at low calcium ion concentrations. For purposes of comparison, hexaethoxy nonylphenyl was evaluated and found to be devoid of calcium binding ability.

EXAMPLE 7

The following represent typical formulations useful as detergent compositions:

| | Percent | | |
| --- | --- | --- | --- |
| | A | B | C |
| Solid | | | |
| compound of Example 4 | 50 | 30 | 35 |
| sodium tripolyhosphate | — | 20 | — |
| sodium silicate (Na$_2$O:SiO$_2$ = 1:2.5) | 6 | 6 | 6 |
| LAS (linear alkylbenzene sulfonate) | — | — | 15 |
| sodium carboxymethyl cellulose | 0.3 | 0.3 | 0.3 |
| sodium sulfate | 13 | 13 | 13 |
| fluorescent dye | 0.16 | 0.16 | 0.16 |
| water | 8 | 8 | 8 |
| miscellaneous | balance | → | → |
| Liquid | | | |
| compound of Example 4 | 30 | 18 | 21 |
| tetrapotassium pyrophosphate | — | 12 | — |
| sodium silicate (Na$_2$O:SiO$_2$ = 1:1.6) | 3.8 | 3.8 | 3.8 |
| LAS | — | — | 9 |
| sodium carboxymethyl cellulose | 0.3 | 0.3 | 0.3 |
| perfume | 0.2 | 0.2 | 0.2 |
| water | 65.7 | 65.7 | 65.7 |

What is claimed is:

1. A compound of formula I:

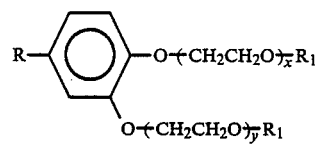

wherein

R is C$_8$–C$>$ straight or branched chain alkyl or alkenyl;

each R$_1$, independently, is hydrogen or a group —R$_2$COOM, where R$_2$ is C$_{1-3}$ alkylene and M is hydrogen, an alkali metal cation, an alkaline earth metal cation or ammonium; and each of x and y is, independently, an integer 1 to 49; with the provisos that: (1) at least one of the R$_1$'s is a group —R$_2$COOM; and (2) the sum of x and y is 3 to 50.

2. A compound according to claim 1 of formula Ia:

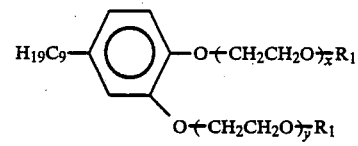

wherein

R' is C$_8$–C$_{22}$ straight or branched chain alkyl;

each R$_1$', independently, is hydrogen or a group —R2COOM, where R$_2$ is —CH2—, —CH$_2$CH$_2$— or —CH$_2$CH$_2$CH$_2$— and M is hydrogen, an alkali metal or ammonium; and each of x' and y' is, independently, an integer 1 to 29; with the provisos that: (1) at least one of the R$_1$'s is a group —R$_2$COOM; and (2) the sum of x' and y' is 3 to 30.

3. A compound according to claim 2 of formula Ib:

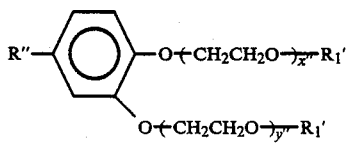

wherein
R″ is $C_8$-$C_{14}$ straight or branched chain alkyl;
each $R_1″$, independently, is hydrogen or a group —$CH_2COOM$, where M is hydrogen, sodium, potassium or ammonium; and
each of x″ and y″ is, independently, an integer 1 to 19; with the provisos that: (1) at least one of the $R_1″$'s is a group —$CH_2COOM$; and (2) the sum of x″ and y″ is 3 to 20.

4. A compound according to claim 3 of formula Ic:

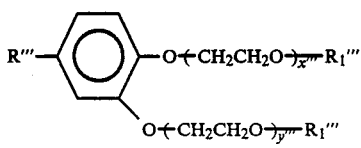

wherein
R‴ is $C_8$-$C_{12}$ straight or branched chain alkyl; each $R_1‴$, independently, is hydrogen or a group —$CH_2COOH$; and
each of x‴ and y‴ is, independently, an integer 1 to 14, with the provisos that: (1) at least one of the $R_1‴$'s is a group —$CH_2COOH$; and (2) the sum of x‴ and y‴ is 3 to 15.

5. A compound according to claim 4 having the formula

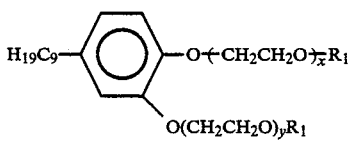

where x+y=12; and the sum of the $R_1$'s=—$CH_2COOH$ (66%); —H (34%).

6. A compound according to claim 4 having the formula

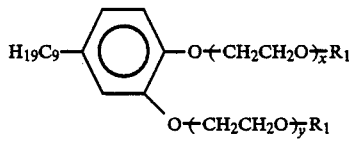

where x+y=3; and the sum of the $R_1$'s=—$CH_2COOH$(47%); —H(53%).

7. A compound according to claim 4 having the formula

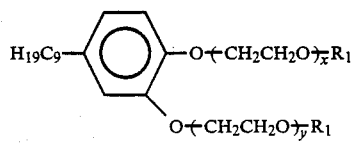

where x+y=6; and the sum of the $R_1$'s=—$CH_2COOH$(52%); —H(48%).

8. A compound according to claim 4 having the formula

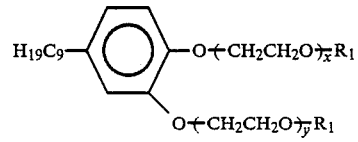

where x+y=9; and the sum of the $R_1$'s =—$CH_2COOH$(58%); —H(42%).

9. A detergent composition comprising, as a self-sequestering surfactant component thereof, from about 5% to about 50% of a compound according to claim 1.

10. A detergent composition according to claim 9 wherein the self-sequestering surfactant component is present in an amount of from 10% to about 50%.

11. A detergent composition according to claim 10 wherein the self-sequestering surfactant component is present in an amount of from 15% to about 50%

12. A detergent composition according to claim 9 comprising, in addition to a self-sequestering surfactant component thereof, an anionic, nonionic, ampholytic or zwitterionic surfactant, or a mixture thereof, said additional surfactant being present in an amount of from about 5% to about 40% by weight of the mixture of the self-sequestering surfactant and additional surfactant.

13. A detergent composition according to claim 12 wherein the additional surfactant is present in an amount of from 10% to about 30% by weight of the mixture of the self-sequestering surfactant and additional surfactant.

14. A detergent composition according to claim 9 comprising, in addition to a self-sequestering surfactant component thereof, a different or separate sequestering compound, said additional sequestering compound being present in an amount of from 5% to about 60% by weight of the mixture of the self-sequestering surfactant and additional sequestering compound.

15. A detergent composition according to claim 14 wherein the additional sequestering compound is present in an amount of from 10% to about 40% by weight of the mixture of the self-sequestering surfactant and additional sequestering compound.

16. A detergent composition according to claim 9 wherein the self-sequestering surfactant component thereof is a compound having the formula

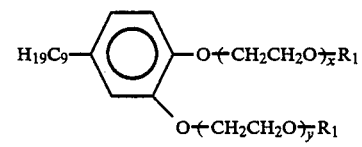

where x+y=12; and the sum of the $R_1$'s=—$CH_2COOH$ (66%); —H (34%).

17. A detergent composition according to claim 9 wherein the self-sequestering surfactant component thereof is a compound having the formula

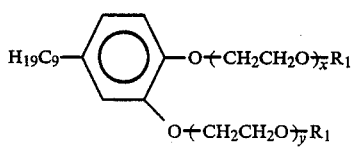

where $x+y=3$; and the sum of the $R_1$'s $= -CH_2COOH(47\%)$; $-H(53\%)$.

18. A detergent composition according to claim 9 wherein the self-sequestering surfactant component thereof is a compound having the formula

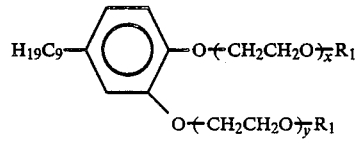

where $x+y=6$; and the sum of the $R_1$'s $= -CH_2COOH(52\%)$; $-H(48\%)$.

19. A detergent composition according to claim 9 wherein the self-sequestering surfactant component thereof is a compound having the formula

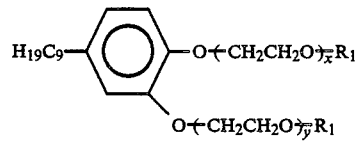

where $x+y=9$; and the sum of the $R_1$'s $= -CH_2COOH(58\%)$; $-H(42\%)$.

* * * * *